(12) United States Patent  (10) Patent No.: US 9,216,033 B2
Feld et al.  (45) Date of Patent: Dec. 22, 2015

(54) SYSTEM AND METHOD FOR TREATING BIOLOGICAL VESSELS

(71) Applicant: QUATTRO VASCULAR PTE LTD., SGX Centre (SG)

(72) Inventors: Tanhum Feld, Moshav Merhavya (IL); Eitan Konstantino, Orinda, CA (US)

(73) Assignee: Quattro Vascular Pte Ltd., Singapore (SG)

( * ) Notice: Subject to any disclaimer, the term of this patent is extended or adjusted under 35 U.S.C. 154(b) by 0 days.

(21) Appl. No.: 13/972,761

(22) Filed: Aug. 21, 2013

(65) Prior Publication Data

US 2014/0066960 A1 Mar. 6, 2014

Related U.S. Application Data

(63) Continuation-in-part of application No. 13/761,525, filed on Feb. 7, 2013.

(60) Provisional application No. 61/596,618, filed on Feb. 8, 2012.

(51) Int. Cl.
*A61B 17/3207* (2006.01)
*A61B 17/50* (2006.01)
*A61M 25/10* (2013.01)
*A61B 17/064* (2006.01)
*A61F 2/06* (2013.01)
*A61B 17/00* (2006.01)

(52) U.S. Cl.
CPC ....... *A61B 17/320725* (2013.01); *A61B 17/064* (2013.01); *A61M 25/104* (2013.01); *A61B 2017/00867* (2013.01); *A61B 2017/0647* (2013.01); *A61M 2025/1084* (2013.01)

(58) Field of Classification Search
CPC .......... A61B 17/320725; A61B 17/50; A61M 2025/1084; A61M 25/104; A61M 2025/1086; A61M 2025/1045; A61F 2/95; A61F 2/958; A61F 2/82; A61F 2/86; A61F 2/89; A61F 2/915; A61F 2/2433; A61F 2002/9505; A61F 2002/9511; A61F 2002/9665; A61F 2002/821; A61F 2002/823; A61F 2002/825; A61F 2002/828; A61F 2002/8483; A61F 2002/8486; A61F 2002/91508; A61F 2002/91516; A61F 2002/91525; A61F 2002/91533; A61F 2002/91541; A61F 2002/9155; A61F 2002/91558; A61F 2002/91575; A61F 2002/91583
USPC ........... 623/1.11, 1.12, 1.23, 2.11; 604/96.01, 604/103, 103.03, 103.05, 103.06, 103.07, 604/103.08, 103.09; 606/108, 191–200, 606/159
See application file for complete search history.

(56) References Cited

U.S. PATENT DOCUMENTS 2,701,559 A  2/1955 Cooper
2,854,983 A  10/1958 Baskin
(Continued)

FOREIGN PATENT DOCUMENTS

CN 1568165 A 1/2005
EP 0 565 796 10/1993
(Continued)

OTHER PUBLICATIONS

International Search Report for Appl. No. PCT/US2011/027982 mailed May 6, 2011 in 3 pages.
(Continued)

*Primary Examiner* — Katrina Stransky
*Assistant Examiner* — Katherine Schwiker
(74) *Attorney, Agent, or Firm* — Knobbe Martens Olson & Bear LLP

(57) ABSTRACT

A system for performing angioplasty and a method of utilizing same are provided. The system includes a balloon mounted on a catheter shaft and an expandable constraining structure mounted over the balloon. The expandable constraining structure includes a plurality of axial struts crossing a plurality of radially-expandable rings being for constraining said balloon such that isolated balloon regions protrude through openings in said constraining structure when the balloon is inflated.

23 Claims, 12 Drawing Sheets

(56) References Cited

U.S. PATENT DOCUMENTS

| | | |
|---|---|---|
| 3,045,677 A | 7/1962 | Wallace |
| 3,467,101 A | 9/1969 | Fogarty et al. |
| 3,825,013 A | 7/1974 | Craven |
| 4,327,736 A | 5/1982 | Inoue |
| 4,456,011 A | 6/1984 | Warnecke |
| 4,483,340 A | 11/1984 | Fogarty et al. |
| 4,637,396 A | 1/1987 | Cook |
| 4,723,549 A | 2/1988 | Wholey et al. |
| 4,796,629 A | 1/1989 | Grayzel |
| 4,921,484 A | 5/1990 | Hillstead |
| 4,976,711 A | 12/1990 | Parins et al. |
| 4,998,539 A | 3/1991 | Delsanti |
| 5,071,407 A | 12/1991 | Porter et al. |
| 5,100,386 A | 3/1992 | Inoue |
| 5,133,732 A | 7/1992 | Wiktor |
| 5,176,693 A | 1/1993 | Pannek |
| 5,181,911 A | 1/1993 | Shturman |
| 5,190,058 A | 3/1993 | Jones et al. |
| 5,196,024 A | 3/1993 | Barath |
| 5,222,971 A | 6/1993 | Willard et al. |
| 5,224,945 A | 7/1993 | Pannek, Jr. |
| 5,263,963 A | 11/1993 | Garrison et al. |
| 5,308,356 A | 5/1994 | Blackshear, Jr. et al. |
| 5,320,634 A | 6/1994 | Vigil et al. |
| 5,336,178 A | 8/1994 | Kaplan |
| 5,336,234 A | 8/1994 | Vigil et al. |
| 5,344,419 A | 9/1994 | Spears |
| 5,449,372 A | 9/1995 | Schmaltz et al. |
| 5,456,666 A | 10/1995 | Campbell et al. |
| 5,456,667 A | 10/1995 | Ham et al. |
| 5,460,607 A | 10/1995 | Miyata et al. |
| 5,501,694 A | 3/1996 | Ressemann et al. |
| 5,527,282 A | 6/1996 | Segal |
| 5,556,408 A | 9/1996 | Farhat |
| 5,562,620 A | 10/1996 | Klein et al. |
| 5,571,086 A | 11/1996 | Kaplan et al. |
| 5,607,442 A | 3/1997 | Fischell et al. |
| 5,609,574 A | 3/1997 | Kaplan et al. |
| 5,616,149 A | 4/1997 | Barath |
| 5,620,457 A | 4/1997 | Pinchasik et al. |
| 5,628,746 A | 5/1997 | Clayman |
| 5,628,755 A | 5/1997 | Heller et al. |
| 5,643,210 A | 7/1997 | Iacob |
| 5,695,469 A | 12/1997 | Segal |
| 5,702,410 A | 12/1997 | Klunder et al. |
| 5,713,863 A | 2/1998 | Vigil et al. |
| 5,730,698 A | 3/1998 | Fischell et al. |
| 5,733,303 A | 3/1998 | Israel et al. |
| 5,735,816 A | 4/1998 | Lieber et al. |
| 5,755,781 A | 5/1998 | Jayaraman |
| 5,772,681 A | 6/1998 | Leoni |
| 5,776,181 A | 7/1998 | Lee et al. |
| 5,797,935 A | 8/1998 | Barath |
| 5,810,767 A | 9/1998 | Klein |
| 5,827,321 A | 10/1998 | Roubin et al. |
| 5,863,284 A | 1/1999 | Klein |
| 5,868,708 A | 2/1999 | Hart et al. |
| 5,868,719 A | 2/1999 | Tsukernik |
| 5,868,779 A | 2/1999 | Ruiz |
| 5,868,783 A | 2/1999 | Tower |
| 5,869,284 A | 2/1999 | Cao et al. |
| 5,904,679 A | 5/1999 | Clayman |
| 5,906,639 A | 5/1999 | Rudnick et al. |
| 5,919,200 A | 7/1999 | Stambaugh et al. |
| 5,961,490 A | 10/1999 | Adams |
| 5,967,984 A | 10/1999 | Chu et al. |
| 5,987,661 A | 11/1999 | Peterson |
| 6,013,055 A | 1/2000 | Bampos et al. |
| 6,036,689 A | 3/2000 | Tu et al. |
| 6,036,708 A | 3/2000 | Sciver |
| 6,053,913 A | 4/2000 | Tu et al. |
| 6,059,811 A | 5/2000 | Pinchasik et al. |
| 6,077,298 A | 6/2000 | Tu et al. |
| 6,102,904 A | 8/2000 | Vigil et al. |
| 6,106,548 A | 8/2000 | Roubin et al. |
| 6,129,706 A | 10/2000 | Janacek |
| 6,156,265 A | 12/2000 | Sugimoto |
| 6,190,403 B1 | 2/2001 | Fischell et al. |
| 6,206,910 B1 | 3/2001 | Berry et al. |
| 6,217,608 B1 | 4/2001 | Penn et al. |
| 6,235,043 B1 | 5/2001 | Reiley et al. |
| 6,241,762 B1 | 6/2001 | Shanley |
| 6,245,040 B1 * | 6/2001 | Inderbitzen et al. ...... 604/103.07 |
| 6,261,319 B1 | 7/2001 | Kveen et al. |
| 6,309,414 B1 | 10/2001 | Rolando et al. |
| 6,319,251 B1 | 11/2001 | Tu et al. |
| 6,361,545 B1 | 3/2002 | Macoviak et al. |
| 6,416,539 B1 | 7/2002 | Hassdenteufel |
| 6,454,775 B1 | 9/2002 | Demarais et al. |
| 6,540,722 B1 | 4/2003 | Boyle et al. |
| 6,605,107 B1 | 8/2003 | Klein |
| 6,616,678 B2 | 9/2003 | Nishtala et al. |
| 6,626,861 B1 | 9/2003 | Hart et al. |
| 6,652,548 B2 | 11/2003 | Evans et al. |
| 6,656,351 B2 | 12/2003 | Boyle |
| 6,695,813 B1 | 2/2004 | Boyle et al. |
| 6,939,320 B2 | 9/2005 | Lennox |
| 6,942,680 B2 | 9/2005 | Grayzel et al. |
| 7,186,237 B2 | 3/2007 | Meyer et al. |
| 7,357,813 B2 | 4/2008 | Burgermeister |
| 7,686,824 B2 | 3/2010 | Konstantino et al. |
| 7,691,119 B2 | 4/2010 | Farnan |
| 7,708,748 B2 | 5/2010 | Weisenburgh, II et al. |
| 7,931,663 B2 | 4/2011 | Farnan et al. |
| 8,388,573 B1 * | 3/2013 | Cox ........................ 604/103.01 |
| 2003/0023200 A1 | 1/2003 | Barbut et al. |
| 2003/0040790 A1* | 2/2003 | Furst .............................. 623/1.11 |
| 2003/0078606 A1 | 4/2003 | Lafontaine et al. |
| 2003/0114915 A1 | 6/2003 | Mareiro et al. |
| 2003/0153870 A1 | 8/2003 | Meyer et al. |
| 2003/0195609 A1 | 10/2003 | Berenstein et al. |
| 2004/0034384 A1 | 2/2004 | Fukaya |
| 2004/0143287 A1 | 7/2004 | Konstantino et al. |
| 2004/0210299 A1 | 10/2004 | Rogers et al. |
| 2004/0230293 A1 | 11/2004 | Yip et al. |
| 2005/0271844 A1 | 12/2005 | Mapes et al. |
| 2006/0015133 A1* | 1/2006 | Grayzel et al. ................ 606/192 |
| 2006/0085025 A1 | 4/2006 | Farnan et al. |
| 2006/0271093 A1 | 11/2006 | Holman et al. |
| 2007/0073376 A1 * | 3/2007 | Krolik et al. ................. 623/1.11 |
| 2009/0105686 A1 | 4/2009 | Snow et al. |
| 2009/0227949 A1* | 9/2009 | Knapp et al. ............. 604/103.02 |
| 2010/0042121 A1 | 2/2010 | Schneider et al. |
| 2011/0071616 A1 | 3/2011 | Clarke et al. |
| 2012/0059401 A1 | 3/2012 | Konstantino et al. |
| 2013/0116655 A1* | 5/2013 | Bacino et al. ................. 604/509 |
| 2013/0211381 A1 | 8/2013 | Feld |
| 2013/0218181 A1 | 8/2013 | Feld et al. |

FOREIGN PATENT DOCUMENTS

| | | |
|---|---|---|
| EP | 0 623 315 | 11/1994 |
| EP | 0 832 608 | 4/1998 |
| EP | 1 042 997 | 10/2000 |
| WO | WO 98/05377 | 2/1998 |
| WO | WO 98/50101 | 11/1998 |
| WO | WO 2011/112863 | 9/2011 |
| WO | WO 2013/119735 | 2/2013 |
| WO | WO 2013/114201 | 8/2013 |

OTHER PUBLICATIONS

International Search Report for Appl. No. PCT/IB13/00217, mailed Jun. 14, 2013 in 7 pages.
International Search Report for Appl. No. PCT/US13/25032, mailed Apr. 19, 2013 in 8 pages.

\* cited by examiner

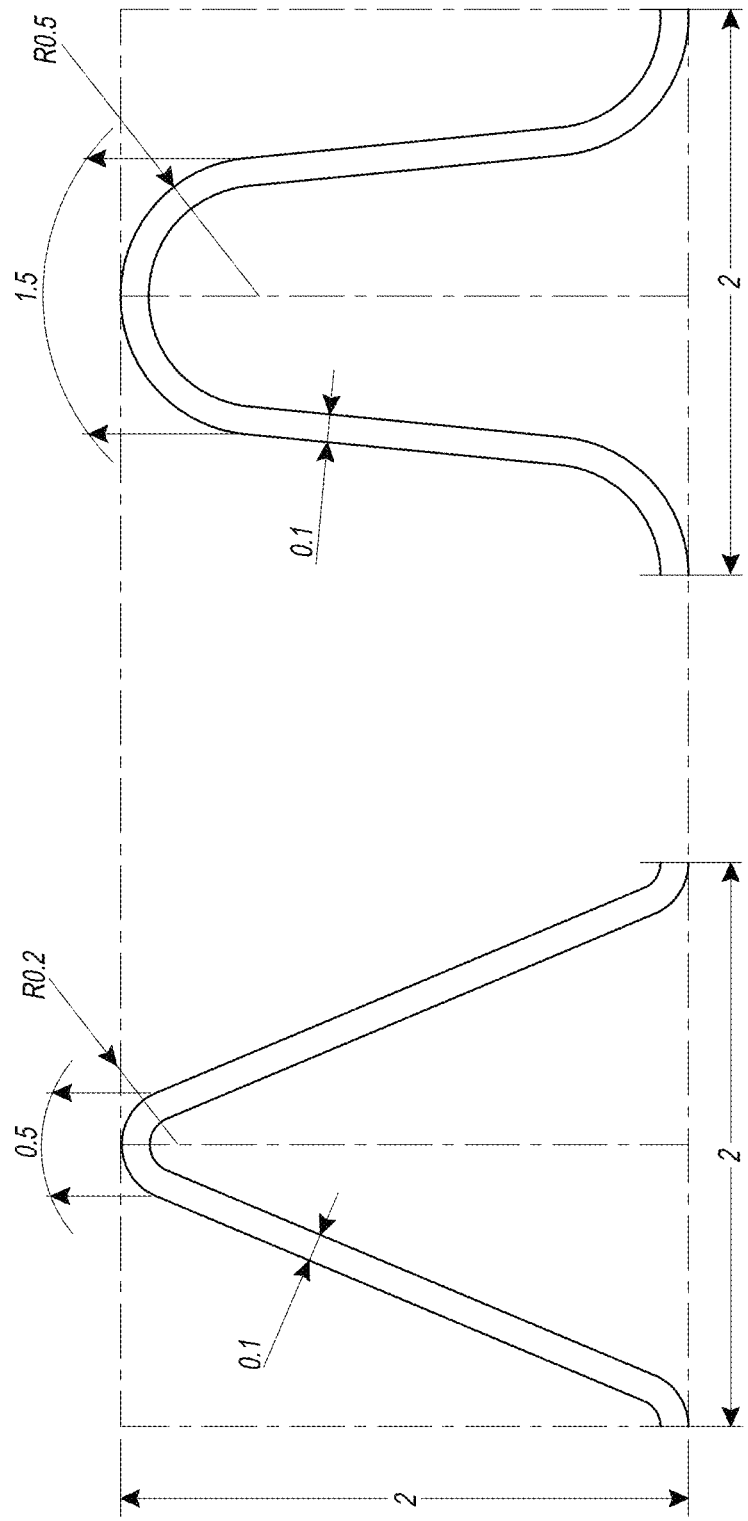

SYSTEM AND METHOD FOR TREATING BIOLOGICAL VESSELS

INCORPORATION BY REFERENCE TO ANY PRIORITY APPLICATIONS

This is a Continuation-in-Part of U.S. patent application Ser. No. 13/761,525 filed on Feb. 7, 2013, which claims the benefit of U.S. Provisional Application No. 61/596,618, filed Feb. 8, 2012, the entireties of both of which are incorporated by reference herein.

BACKGROUND OF THE INVENTION

1. Field of the Invention

The present invention relates to a system and method for treating biological vessels and, more particularly, to an angioplasty balloon catheter having an expandable constraining structure positioned over the balloon and configured for constraining balloon inflation thereby enabling isolated balloon regions to protrude from the constraining structure during inflation.

2. Description of the Related Art

Percutaneous transluminal angioplasty (PTA) is a procedure in which a balloon catheter is inserted through an artery and guided to the region of lumen narrowing. The balloon is inflated to force the plaque material (typically fat and calcium) against the wall of the artery to open the vessel lumen and improve blood flow.

Angioplasty balloons are typically cylindrical when inflated and have different lengths and diameters to conform to different vessel sizes. The balloons are inflated at high pressure, normally between 8-20 atmospheres, in order to overcome the resistance of the plaque and achieve luminal expansion.

High pressure angioplasty is often traumatic to the vessel walls and can lead to vessel wall dissections. Such dissections are common and can be severe and may require urgent surgery or placement of stents. In addition, dissection may contribute to poor long term clinical results and restenosis even if a stent is placed in the treated lesion.

Dissections are usually attributed to several mechanisms occurring during balloon inflation including shear forces applied on the vessel walls as the balloon pleats unfold as well as uneven balloon inflation which occurs as a result of the non-symmetric nature of the vascular disease.

Shear forces result from balloon unfolding and an increase in balloon diameter in the radial direction as the folded balloon unwraps. As the folded pleats of the balloon open, the layers slide over one another and apply tangential forces to the lesion and/or vessel wall which can abrade the lesion or vascular wall and in the worst instances cause dissections.

Uneven inflation results from the uneven nature of the disease in the vessel. Angioplasty balloons are commonly non-compliant or semi-compliant, and when semi-compliant balloons are inflated against an eccentric lesion, the balloon will follow the "path of least resistance" and its diameter will increase more in the less diseased sections of the vessel (causing a dog bone effect), often increasing trauma in these areas.

Due to the above limitations, standard balloon catheters are also incapable of applying local forces sufficient to open to resistant plaque regions and thus can be ineffective in providing ample patency in highly calcified lesions, such as those prevalent in peripheral arteries.

Attempts to solve the above limitations of balloon catheters by increasing local forces via cutting or scoring elements (blades/wires) positioned on the balloon surface (e.g. US20040143287 and US20060085025) were somewhat successful at opening resistant lesions but did not adequately solve the aforementioned problems resulting from balloon unfolding and uneven inflation.

Thus it would be highly advantageous to have an angioplasty balloon catheter configured for minimizing trauma and dissection to the blood vessel walls as the balloon is inflated as well as for enabling application of local forces to discrete lesion regions that are resistant to opening.

SUMMARY OF THE INVENTION

According to one aspect of the present invention, there is provided a system for performing angioplasty comprising: (a) a balloon mounted on a catheter shaft; and (b) an expandable constraining structure including a plurality of axial struts crossing a plurality of radially-expandable rings, for constraining the balloon such that isolated balloon regions protrude through openings in the constraining structure when the balloon is inflated; the expandable constraining structure being configured such that radial expansion of the radially-expandable rings does not substantially alter a distance between adjacent radially-expandable rings.

According to further features in preferred embodiments of the invention described below, the expandable constraining structure is also configured such that radial expansion of the radially-expandable rings moves adjacent axial struts attached to the adjacent radially-expandable rings in opposite (axial) directions.

According to still further features in the described preferred embodiments, the radially-expandable rings are configured with peaks and valleys forming an undulating omega loop path.

According to still further features in the described preferred embodiments, the plurality of axial struts interconnect the plurality of radially-expandable rings at the peaks and the valleys.

According to still further features in the described preferred embodiments, the system comprises at least 4 axial struts crossing at least 4 radially-expandable rings forming at least 16 of the openings.

According to still further features in the described preferred embodiments, the expandable constraining structure further includes first and second end rings for fixedly attaching the expandable constraining structure to the catheter.

According to still further features in the described preferred embodiments, the first and second rings are connected to terminal radially-expandable rings via N end struts, N being half of a number of the plurality of axial struts.

According to still further features in the described preferred embodiments, the N end struts of the first end ring are connected to peaks of a first terminal radially-expandable ring, and the N end struts of the second end ring are connected to valleys of a second terminal radially-expandable ring.

According to still further features in the described preferred embodiments, the N end struts of the first end ring are connected to peaks of a first terminal radially-expandable ring, and the N end struts of the second end ring are connected to peaks of a second terminal radially-expandable ring.

According to still further features in the described preferred embodiments, N may be 2 or 3 or 4.

According to still further features in the described preferred embodiments, the plurality of axial struts are fabricated from a super-elastic alloy having a thickness of from about 0.04 to about 0.12 mm.

According to still further features in the described preferred embodiments, the plurality of radially-expandable rings are fabricated from a super-elastic alloy having a thickness of about 0.05 to about 0.12 mm.

According to still further features in the described preferred embodiments, the plurality of radially-expandable rings are capable of radially expanding from a compressed state of about 1 mm to an expanded state of at least about 5 mm and in some embodiments about 6 mm in diameter, or from a compressed state of 2 mm to an expanded state of at least about 8 or 10 mm and in some embodiments 12 mm in diameter. In any case, the radially expandable rings have an expanded diameter which is smaller than that of the inflated balloon in order to enable the balloon to protrude through the constraining structure and form the pillow-like structures described herein.

According to still further features in the described preferred embodiments, the plurality of radially-expandable form an undulating radial path when compressed and a linear radial path when expanded.

According to still further features in the described preferred embodiments, a length of the expandable constraining structure from the first end ring to the second end ring is 10-300 mm.

According to still further features in the described preferred embodiments, each omega loop of the undulating omega loop path is composed of two contiguous sine curves.

According to still further features in the described preferred embodiments, the sine curve has a radius of 0.3-0.5 mm, such as at least about 0.35 mm or at least about 0.45 mm.

According to still further features in the described preferred embodiments, the isolated balloon regions protrude about 0.1-0.7 mm from the radially outwardly facing surface of the expandable constraining structure, such as at least about 0.3 mm, and preferably at least about 0.6 mm.

According to still further features in the described preferred embodiments, the balloon is coated with a drug coating, which may also contain an excipient or excipients. The excipient is an inactive substance that serves as the vehicle or medium for an active drug substance.

According to still further features in the described preferred embodiments, the drug coating is applied on the isolated balloon regions that protrude through the openings.

According to still further features in the described preferred embodiments, the isolated balloon regions protruding through the openings are rectangular.

According to still further features in the described preferred embodiments, the isolated balloon regions protruding through the openings are about 1-5 mm in length and 1-3.5 mm in width.

According to another aspect of the present invention, there is provided a method of treating a body vessel comprising: (a) positioning, in the vessel, a balloon disposed within an expandable constraining structure including a plurality of axial struts crossing a plurality of radially-expandable rings being for constraining the balloon such that isolated balloon regions protrude through openings in the expandable constraining structure when the balloon is inflated; the expandable constraining structure being configured such that radial expansion of the radially-expandable rings: (i) does not substantially alter a distance between adjacent radially-expandable rings; and (ii) axially moves adjacent axial struts attached to the adjacent radially-expandable rings in opposite directions; and (b) inflating the balloon so as to enable the isolated balloon regions to protrude through the openings and contact a wall of the vessel while the plurality of axial struts and the plurality of radially-expandable rings are displaced from the vessel, thereby treating the body vessel.

According to still further features in the described preferred embodiments, (b) is effected by inflating the balloon to at least 3 atm.

According to still further features in the described preferred embodiments, the vessel is an artery and the treatment is angioplasty.

According to another aspect of the present invention there is provided a medical prosthesis comprising a substantially tubular expandable structure including a plurality of axial struts crossing a plurality of radially-expandable rings, the expandable constraining structure being configured such that radial expansion of the radially-expandable rings: (a) does not substantially alter a distance between adjacent radially-expandable rings; and (b) axially moves adjacent axial struts attached to the adjacent radially-expandable rings in opposite directions.

The present invention successfully addresses the shortcomings of the presently known configurations by providing a balloon catheter that includes a cage-like constraining structure designed for minimizing dissection-inducing stresses on the vessel wall while enabling localized high pressure treatment of dilation-resistant lesion regions.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

FIGS. 4a-b schematically illustrate a ring loop having a small radius of curvature (FIG. 4a) and a ring having a loop with a relatively large radius of curvature (FIG. 4b).

DETAILED DESCRIPTION OF THE PREFERRED EMBODIMENT

Figure 1A:
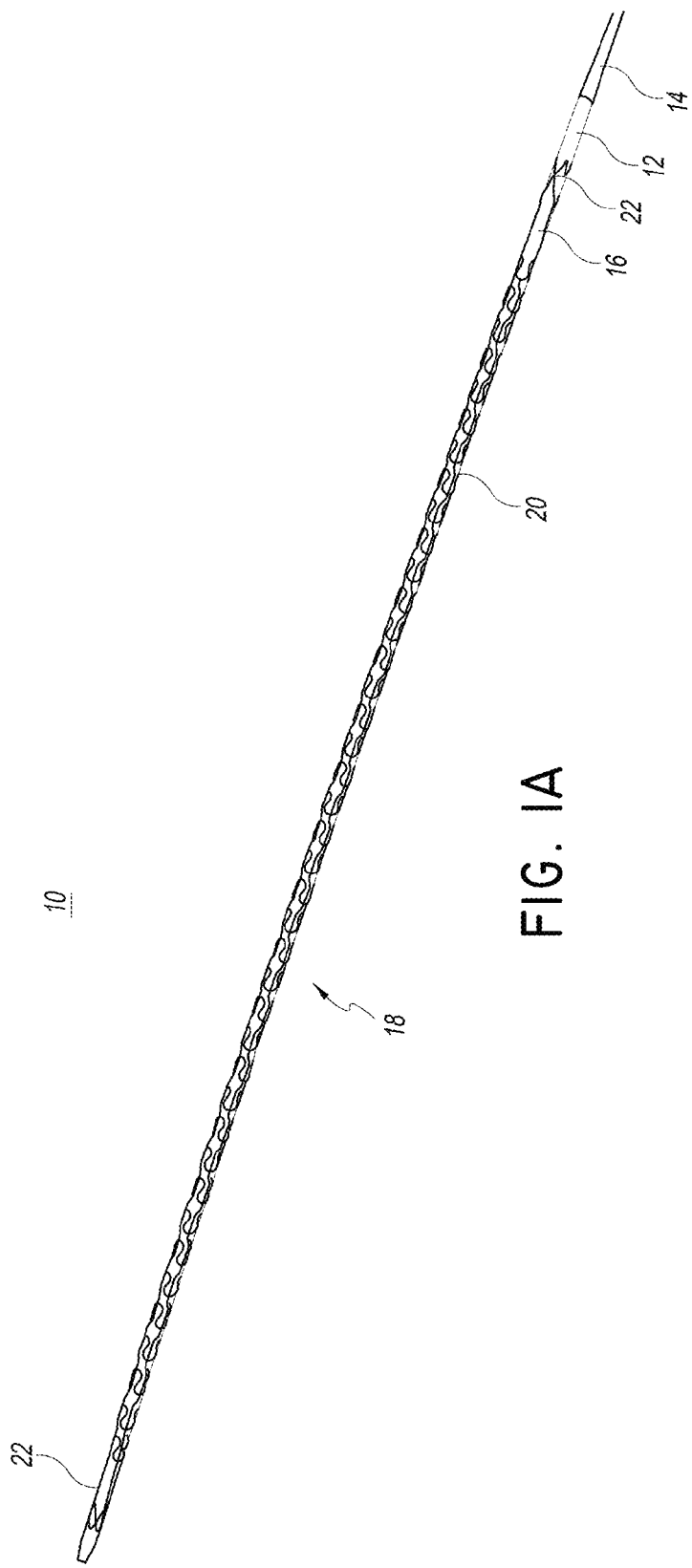
FIGS. 1a-b illustrate one embodiment of the present system in a non-inflated configuration (FIG. 1a) and in an inflated configuration (FIG. 1b) showing protrusion of isolated balloon regions.

The present invention relates to a balloon catheter system which can be used to open stenosed vessel region while minimizing vessel wall trauma and dissections and providing localized forces to discrete lesion regions and a homogeneous distribution of forces along the lesion.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein are for the purpose of description and should not be regarded as limiting.

Attempts to traverse the limitations of standard angioplasty balloon catheters using cutting or scoring elements have met with limited clinical success.

In a previously filed patent application (U.S. patent application Ser. No. 13/044,425, filed Mar. 9, 2011, the entire disclosure of which is hereby incorporated by reference), the present inventors described a balloon catheter that includes an expandable constraining structure (CS) positioned over an angioplasty balloon. The constraining structure was configured such that when the balloon was inflated to a diameter larger than that of the expandable constraining structure, isolated balloon regions protruded from openings in the expandable constraining structure. Such a unique configuration protected the vessel wall from the effects of balloon unfolding and uneven inflation while also enabled application of localized forces to a discrete plaque region.

In order to enable a delivery state and expansion in the vessel (and enable isolated balloon regions to protrude therethrough), the expandable constraining structure of U.S. patent application Ser. No. 13/044,425 is preferably constructed from several axial struts crossing several radially-expandable rings (forming a cage with balloon openings). The radially expandable rings must be compressed for delivery and expanded for operability and should preferably assume a linear circumferential configuration when expanded such that isolated balloon regions protruding through the expandable constraining structure contact substantially linear surfaces.

Thus, the operability of the expandable constraining structure, and in particular its ability to compress and expand without applying excessive strain to its structural elements and upon the balloon, largely depends on the radially expandable rings and connection therebetween.

Expansion through large diameter ranges can strain the struts and rings, leading to ring failure or strut deformation (see Example section).

Thus, the present inventors continued to experiment with various expandable constraining structure designs, and particularly with various radially expandable rings designs, in efforts to improve the operability of the expandable constraining structure.

As is described hereunder and in the Examples section which follows, the present inventors have devised a radially expandable ring configuration that substantially enhances the operability of the expandable constraining structure.

Thus, according to one aspect of the present invention there is provided a system for performing angioplasty in a subject (e.g. a human subject).

The system includes a balloon mounted on a catheter shaft and an expandable constraining structure mounted over the balloon (in a coaxial arrangement), and fixedly attached at its distal and proximal ends to the catheter shaft.

The catheter can be any catheter configuration suitable for use in angioplasty procedures. The catheter can be configured for over-the-wire or a rapid exchange delivery and can include suitable connectors for wire insertion, inflation and the like at its proximal end. The catheter shaft can be any length and diameter suitable for angioplasty of peripheral, coronary or cerebral blood vessels. Suitable lengths (L) and diameters (D) can be in the range of about 5-30 mm L, 2-5 mm D for coronary applications and 20-300 mm L, 2-12 or more) mm D for peripheral vessels applications.

The balloon can be a compliant, a semi-compliant or a non-complaint balloon fabricated from nylon, Pebax and the like at dimensions selected from a range of about 5-300 mm in length and about 2-12 (or more) mm in diameter. The balloon can be cylindrical, or any other shape known in the art.

The expandable constraining structure includes a plurality of axial struts crossing a plurality of radially-expandable rings. The struts and rings form a cage-like structure that expands with balloon expansion, but constrains the balloon such that isolated balloon regions protrude through openings in the cage structure when the balloon is inflated therein.

Thus, the expandable constraining structure provides protection of vessel wall/plaque from shear forces caused by balloon unfolding, protection from uneven expansion during radial dilatation, and strain relief zones through isolated balloon protrusions.

The expandable constraining structure is configured such that radial expansion of the radially-expandable rings does not substantially alter a distance between any two axially adjacent rings while shifting circumferentially-adjacent axial struts (interconnecting the two adjacent rings) in opposite directions (e.g., one strut shifts in a proximal direction, while its circumferentially-adjacent strut shifts in a distal direction).

Such an expansion profile can provide several advantages:

(i) the radially expandable rings do not substantially shift axially with respect to the balloon and thus do not apply frictional forces thereto during inflation;

(ii) such an expandable constraining structure can be configured such that its length increases, decreases or remains constant during expansion; since balloons can also change during inflation, such a feature can further reduce strain on the expandable constraining structure and/or balloon; and (iii) expandable constraining structure can match changes in length of the balloon during inflation, thus enabling fixedly attaching the CS to the catheter shaft on both sides of the balloon without a need for length compensation design elements.

FIGS. 1a-3c illustrate angioplasty systems that include expandable constraining structures constructed in accordance with the teachings of the present invention.

Figure 1B:
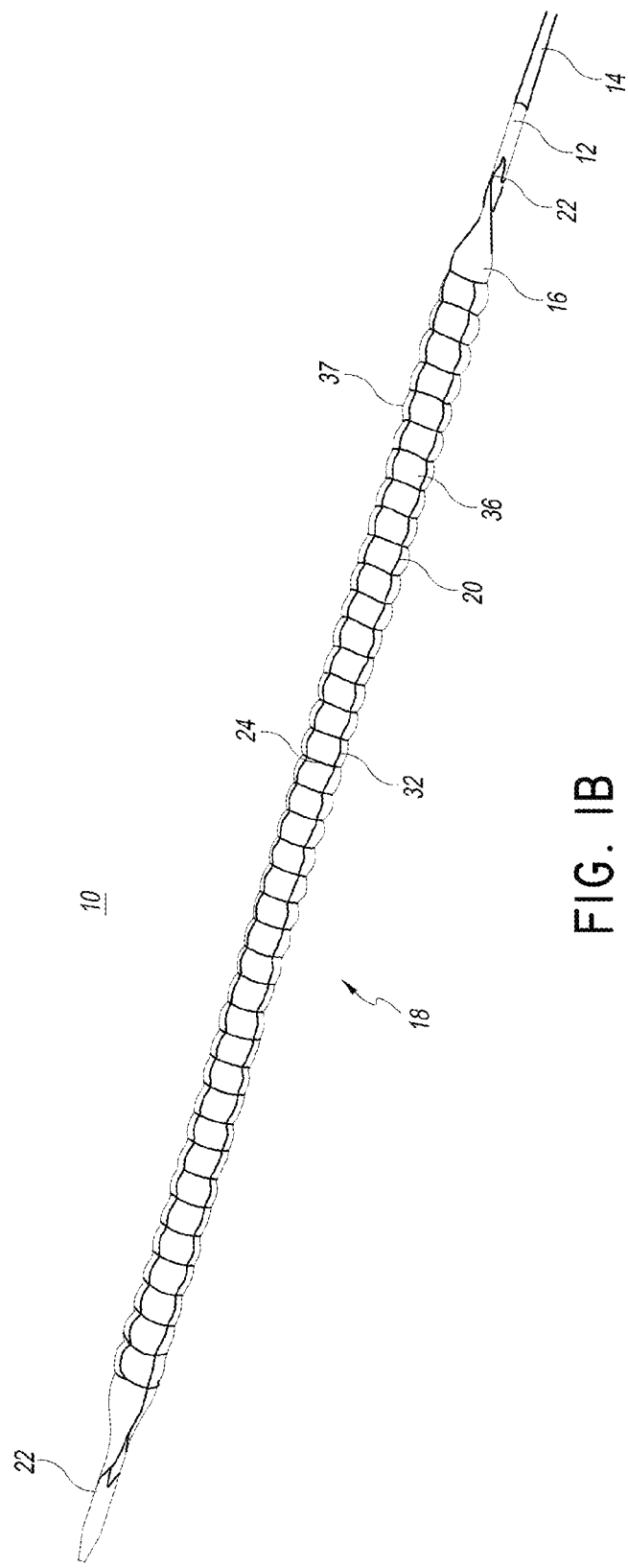

Referring now to the drawings, FIGS. 1a-b illustrate one embodiment of an angioplasty system which is referred to herein as system 10. FIG. 1a illustrates a system 10 in a collapsed (delivery) configuration, while FIG. 1b illustrates system 10 in an expanded configuration.

System 10 includes a catheter 12 having a shaft 14 which is fabricated from one or more concentrically arranged hollow tubes (typically 3) fabricated from a polymer such as Nylon, Pebax, HDPE, LDPE, PTFE, Polyimide and the like. A balloon 16 is mounted on a distal end region 18 of shaft 14 and is inflatable via an inflation lumen that extends the length of shaft 14 from balloon 16 to a handle/connector (not shown) of system 10 mounted on the proximal end of shaft 14. Balloon 16 is fabricated and bonded onto shaft 14 using well known prior art approaches.

Figure 2A:
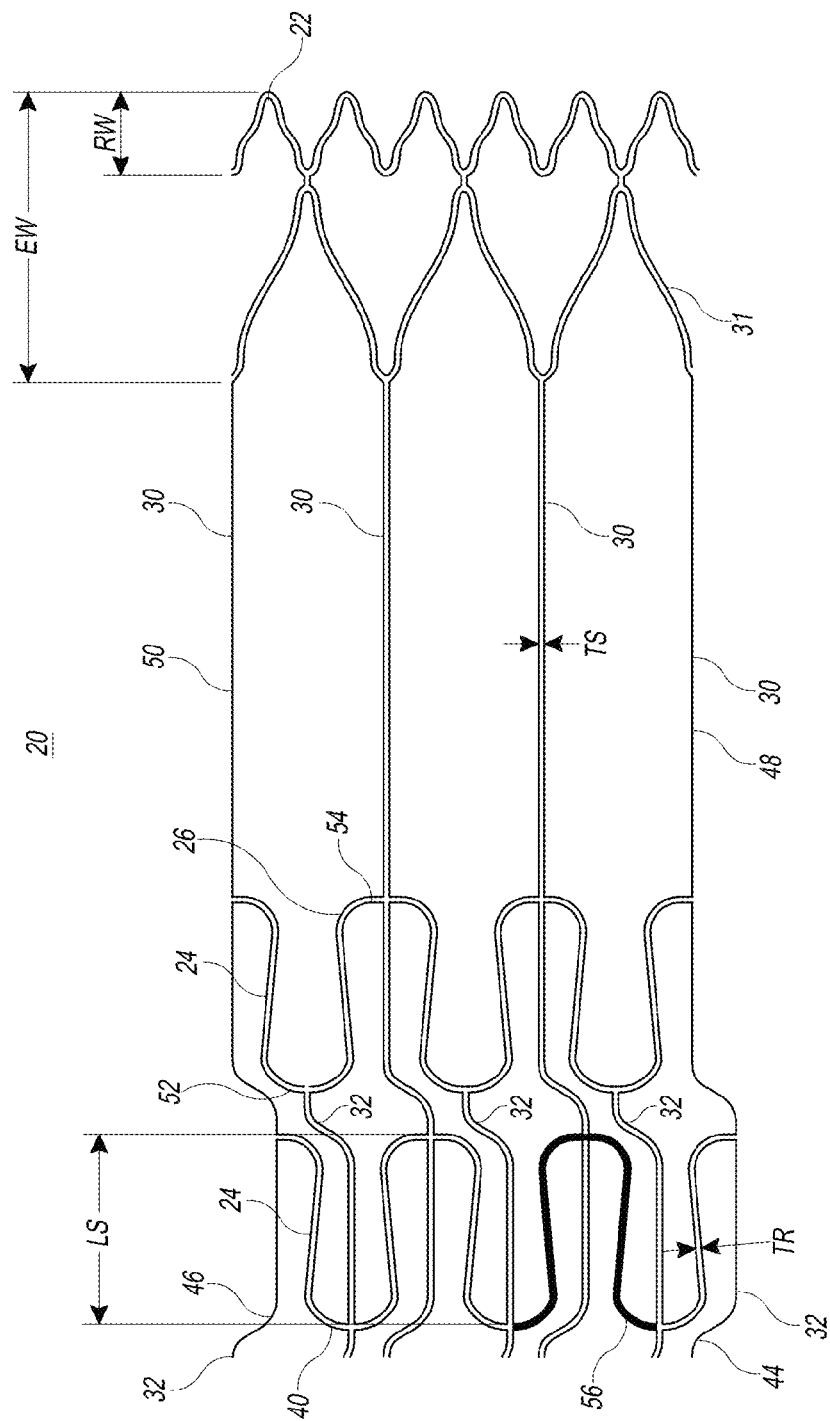
FIG. 2a is a drawing of one end of the constraining structure in a magnified view containing 2 rings and one end crown of the CS when the CS is not expanded by the balloon.

An expandable constraining structure 20 (referred to hereunder as CS 20, a portion of which is shown separately in FIG. 2a) which is tubular in shape is mounted over balloon 16 in a co-axial arrangement. CS 20 is fixedly attached with respect to shaft 14 via two end rings 22, each being connected to a terminal radially expandable ring 24 (proximal ring—26, distal ring—28) of CS 20 via one or more end struts 30. The region of CS 20 encapsulating balloon 16 includes a plurality of axial struts 32 [also referred to herein as strut(s) 32] crossing a plurality of radially expandable rings 24 [also referred to herein as ring(s) 24]. Rings 24 and struts 32 form a grid with opening 34 through which isolated balloon region 36 protrude (0.2-0.7 mm above the surface of CS 20) upon inflation of the balloon to a pressure of 2-3 atmospheres or more and form pillow like structures 37 of 0.2-3.5 mm (preferably 1-3 mm) in length and width (FIG. 1b) with rings 24 and struts 32 forming depressions therebetween. Such pillow-like structures 37 are formed upon inflation since CS 20 expands to a diameter which is less than the diameter of the inflated balloon 16.

CS 20 can be fabricated from welded superelastic wire (having a round or rectangular profile), or it can be laser cut from a tube/sheet. Rings 24 and struts 32 can be fabricated from a superelastic alloy such as Nitinol and have a thickness of 0.04 to 0.12 mm (indicated by TR and TS in FIG. 2a).

Any number of rings 24/struts 32 can be used in CS 20. For example, CS 20 can include a number of rings 24, e.g. 4-80 and 2-6 struts 32. The number of rings 24 can be determined by the balloon length divided by two or three. Forty rings 24 and 4 struts 32 are shown in FIGS. 1a-b for an 80 mm length balloon. The number of rings 24, and to a lesser degree struts 32 used in CS 20, can depend on the application (type of vessel) and diameter of vessel treated, and the length of balloon 16 used. For example, in peripheral angioplasty, system 10 can utilize a balloon having a diameter of 3.0 mm and length of 80 mm and, as such, can include a CS 20 having 4 struts 32 and about 40 rings 24, resulting in 156 openings 34. Generally a CS 20 having 8-400 openings 34 can be formed, such as at least about 50, in some embodiments at least about 100 or 200. When used in angioplasty, the length of isolated balloon regions 36 is preferably selected so as to enable application of an inflation force to discrete stenosed regions 5-30 mm in length and 2.0-12.0 mm in diameter. Thus, in such cases, the length of balloon 16 dictates the number of rings 24. The CS will typically create at least about 1, at least about 1.5 and in some implementations at least about 1.75 pillows in the inflated balloon per 1 mm of inflated balloon, length, depending upon desired clinical performance.

As is mentioned hereinabove rings 24 have a unique structure and unique strut 32 interconnections.

FIG. 2a is a magnified flat view of 2 rings 24 (proximal terminal ring 26 and adjacent ring 40) and portions of 4 struts 32 that interconnect rings 24 when CS is collapsed (for delivery). Since CS 20 is a cylinder, it is flattened for the purpose of illustration by separating strut 32 into halves 44 and 46. FIG. 2a also shows end ring 22 (having a width of about 0.25-1.5 mm, indicated by RW in FIG. 2a) which is connected to ring 26 through angled couplers 31 (three triangular-shaped couplers shown) and three end struts 30 (one end strut 30 separated into halves 48 and 50). The width of end ring 22 and attached couplers 31 can be about 1.5-6 mm (indicated by EW in FIG. 2a).

In the collapsed configuration, rings 24 are preferably configured with peaks 52 and valleys 54 (peaks 52 face left in the Figures) forming an undulating omega loop 56 (one omega loop 56 emphasized in FIG. 2a) path. Peaks 52 and valleys 54 are curved to facilitate linearization of omega loops 56 during expansion of CS 20. The path between peak 52 and valley 54 of two contiguous omega loops 56 forms a sine wave/curve.

Figure 2B:
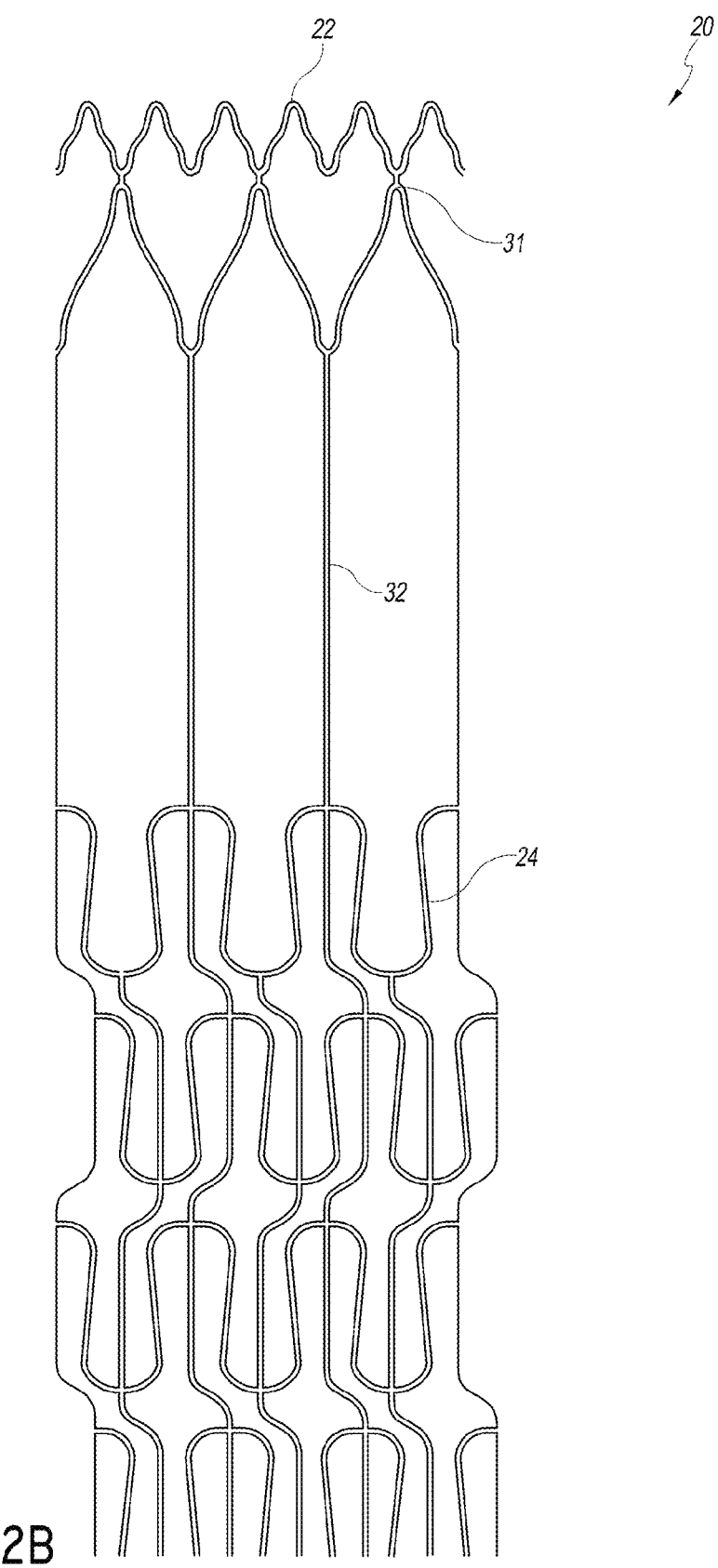
FIGS. 2b-d illustrate one end of the constraining structure while expanding from a collapsed state (FIG. 2b), through a partially expanded state (FIG. 2c) to a fully expanded state (FIGS. 2d).
Figure 2C:
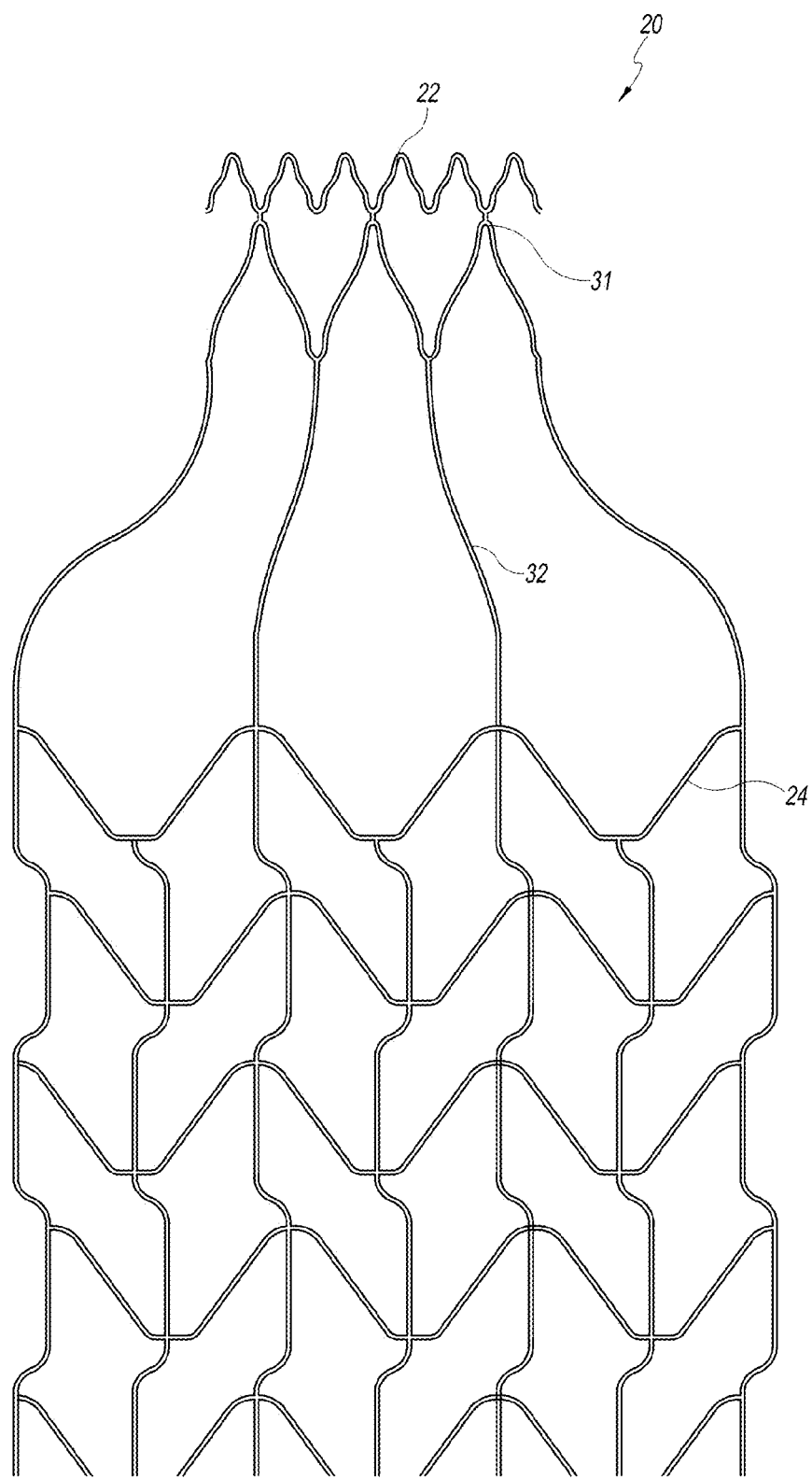
Figure 2D:
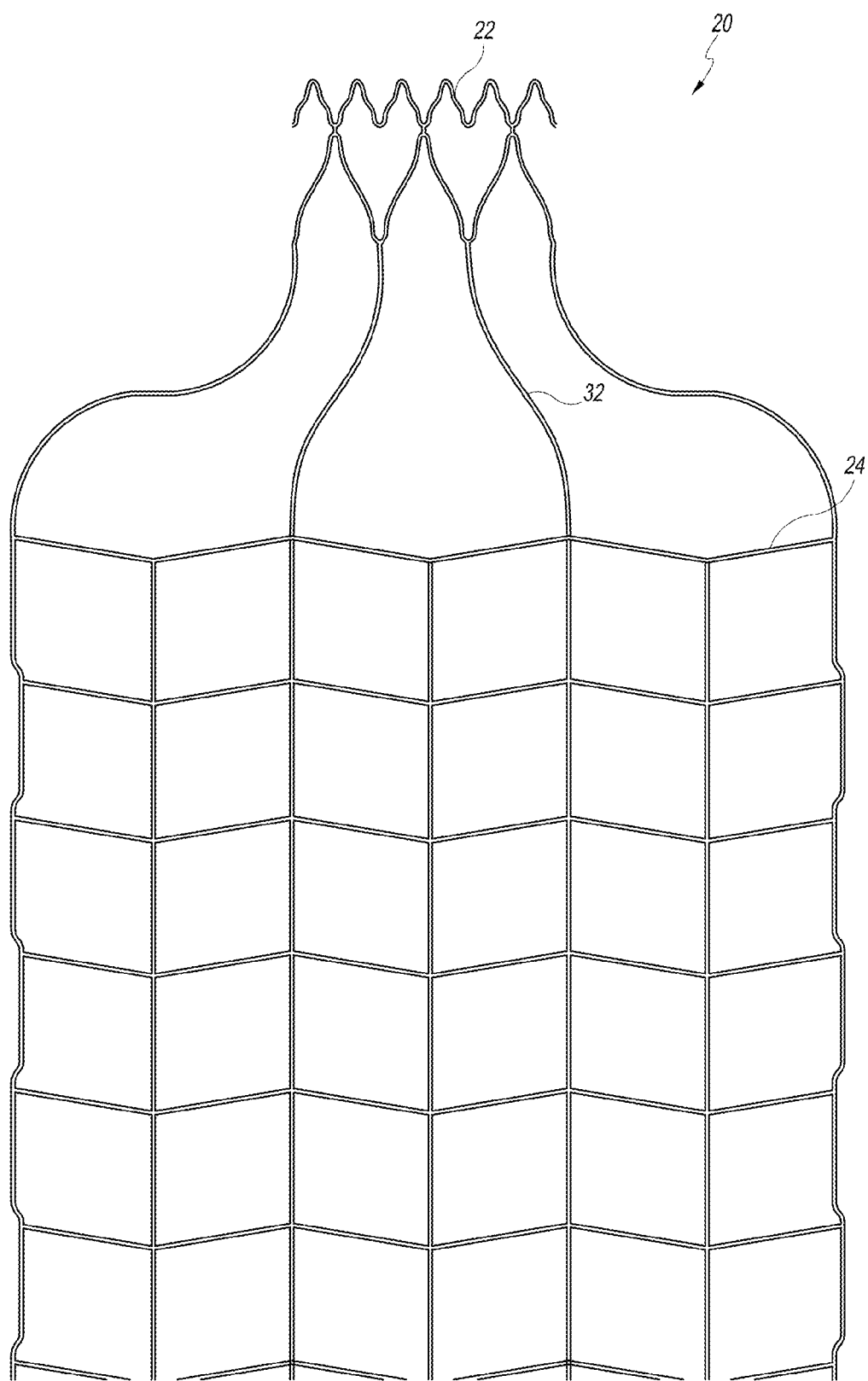

Expansion of ring 24 nearly linearizes each sine curve. Therefore the sine radius has to be large enough in order not to develop high strains in ring 24 and fail. The preferred sine radius is about 0.3-0.5 mm. The overall length of the sine path (darkened line referenced by LS in FIG. 2a) is smaller than the circumference of inflated balloon 16. For example for a 3 mm diameter balloon the circumference is $3 \times \pi$ and the sine length is $2.8 \times \pi$. This length is determined by the strains that form in ring 24 upon inflation (these strains increase with shorter sign length). This sine length is also small enough to form pillow-like structures 37 (between about 0.2 to 0.5 mm in height beyond the radially outwardly facing surface of the adjacent CS). These two parameters (sine length and sine radius) dictate the sine amplitude, in this example (for 3 mm balloon) about 1.4 mm, and also dictate a minimum for the distance between adjacent rings 24. FIGS. 2b-d illustrate expansion of CS 20 showing linearization of rings 24 and struts 32 (to final shape in FIG. 2d) while maintaining distances between adjacent rings 24 and struts 32 substantially unchanged.

Any number of omega loops (e.g., one or two or three or four or more) can be included in ring 24. However, in cases where rings 24 need to tightly fit over a folded balloon 16 in order to accommodate delivery thru tight lesions, the relatively large sine radius and small overall diameter of compressed ring 24 can dictate two sine waves per ring 24 (two peaks 52 and two valleys 54) in a balloon less than 4.5 mm (inflated diameter). A balloon 4.5 mm or larger (inflated diameter) can accommodate three sine waves per ring 24 (three peaks 52 and thereto valleys 54) and can be compressed for delivery to about 1 mm or slightly more (e.g. 1.2 mm).

Struts 32 (four in FIG. 2a) interconnect rings through peaks 52 and valleys 54 (peak-to-peak, valley-to-valley). Struts 32 can follow a linear or slightly undulating path along the length of CS 20. The latter is preferred since rings 24 are more efficiently packed (lengthwise) by circumferentially offsetting peak 52/valleys 54 of adjacent rings 24.

An undulating path (for strut 32) can also be advantageous due to deformation of strut 32 upon expansion of CS 20. The ends of strut 32 are attached to the rings 24 and therefore are forced to the relatively small diameter of the rings 24 on expansion. At the same time, the middle area of strut 32 is being pushed outwardly by the pressure of balloon 16, and thus, strut 32 arcs radially outward. A linear strut 32 would thus shorten upon expansion due to arcing. Such shortening between adjacent rings 24 can then result in shortening of the overall length of CS 20 and generation of high axial compression forces on the balloon. The undulating path of strut 32 mitigates this shortening: as pillows are formed on both sides of strut 32 they apply a force to strut 32 that linearize the strut and mitigates shortening. The magnitude of undulation can control the magnitude of shortening mitigation and can be selected such that the shortening is minimal and distance between rings is kept substantially constant.

As is shown in FIGS. 2b-c, when CS 20 expands (during balloon inflation), peaks 52 and valleys 54 linearize, thereby linearizing omega loops 56 from about 0 degrees to about 180 degrees to form a substantially linear ring 24 (FIG. 2c).

During expansion, adjacent struts 24 (60 and 62 in FIGS. 2a-c) shift in opposite axial directions; this is due to the fact that peaks 52 move in a direction opposite to valleys 54.

As is mentioned hereinabove, CS 20 is attached to catheter shaft 14 either directly, or to the balloon neck overlying the shaft, via two end rings 22 each connected via one or more end struts 30 to a terminal ring 24 (designated 26 and 28). End rings can be connected directly to end struts 30 or through a pair of angled couplers 31 (FIG. 2a). Use of such couplers 31 enables use of shorter end struts 30 thus making these relatively long and thin struts more stable.

The number of end struts 30 (on each side) can be half that of the number of struts 32. For example, in a CS 20 having 4 struts 32 (and any number of rings 24), an end ring 22 is connected to a terminal ring 24 (26 or 28) via 2 struts 30.

End rings 22 can be fixedly attached to shaft 14 preferably via thermal bonding crimping and/or adhesive bonding. End rings 22 are configured as zigzag rings with an amplitude of approximately 1 mm or shorter. End rings 22 are preferably connected via one or more struts 30 to external peaks 52 of terminal ring (26 or 28) although other connection configurations are also contemplated herein.

Since inflation of balloon 16 causes terminal rings 26 and 28 to expand and peaks 52 to linearize, connecting struts 30 (on both sides of CS 20) to a peak 52 of terminal ring 26 and a peak 52 of terminal ring 28 (which is on the same strut 32) can cause buckling (inward or outward arcing) of CS 20 and, as such, it is less preferred. To avoid such buckling, end rings 22 are preferably connected via strut 30 to a peak 52 of one terminal ring (e.g. 26) and a valley 54 of the opposite terminal ring (e.g. 28) in such a configuration that the connection does not span the same lengthwise strut 32.

Figure 3A:
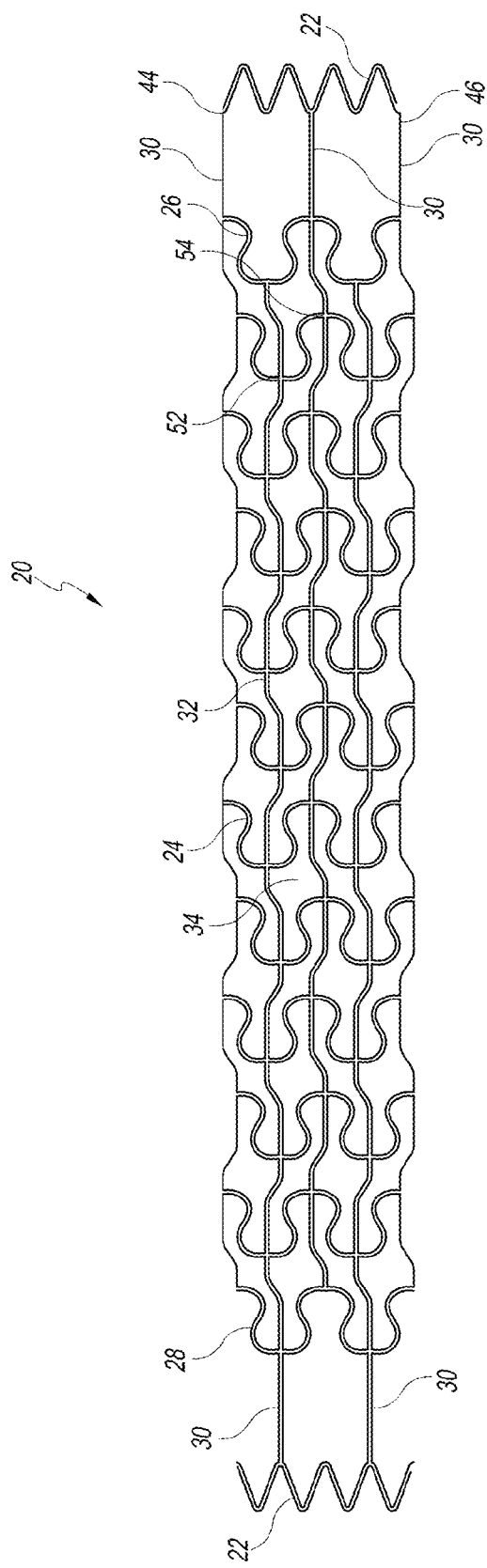
FIGS. 3a-c illustrate a CS having three end strut configurations that lead to: a decrease in CS length (FIG. 3a), an increase in CS length (FIG. 3b) or no change in CS length (FIG. 3c) when the CS is expanded.
Figure 3B:
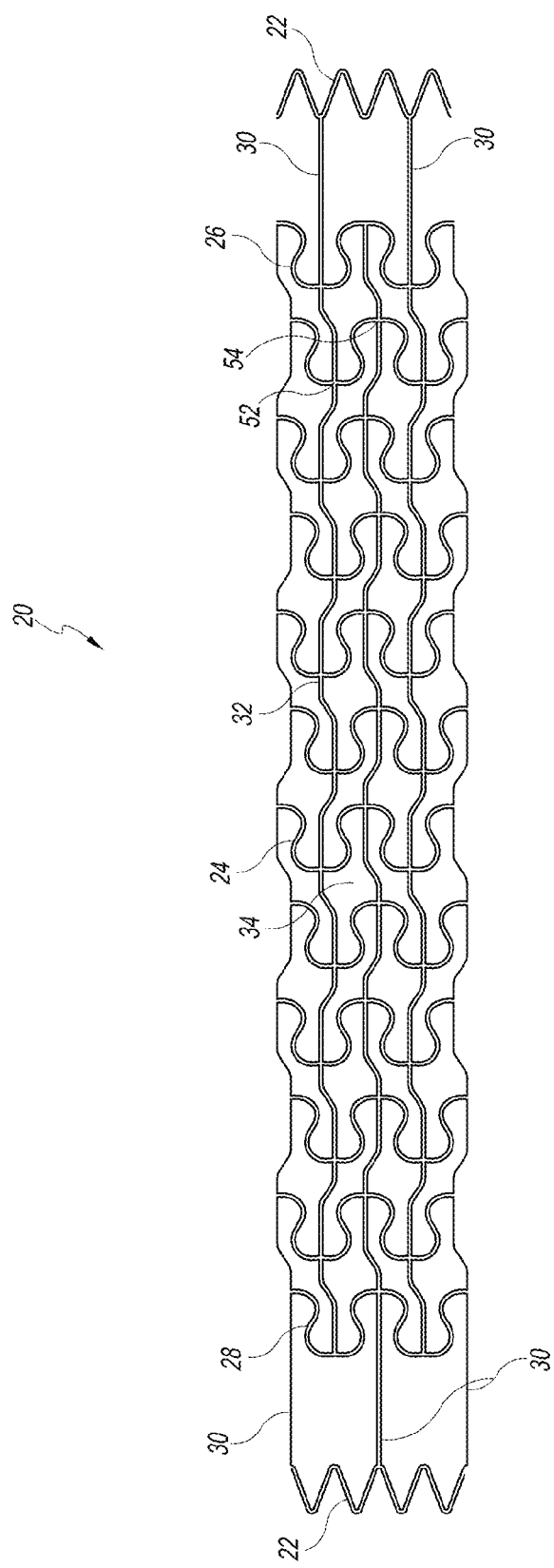
Figure 3C:
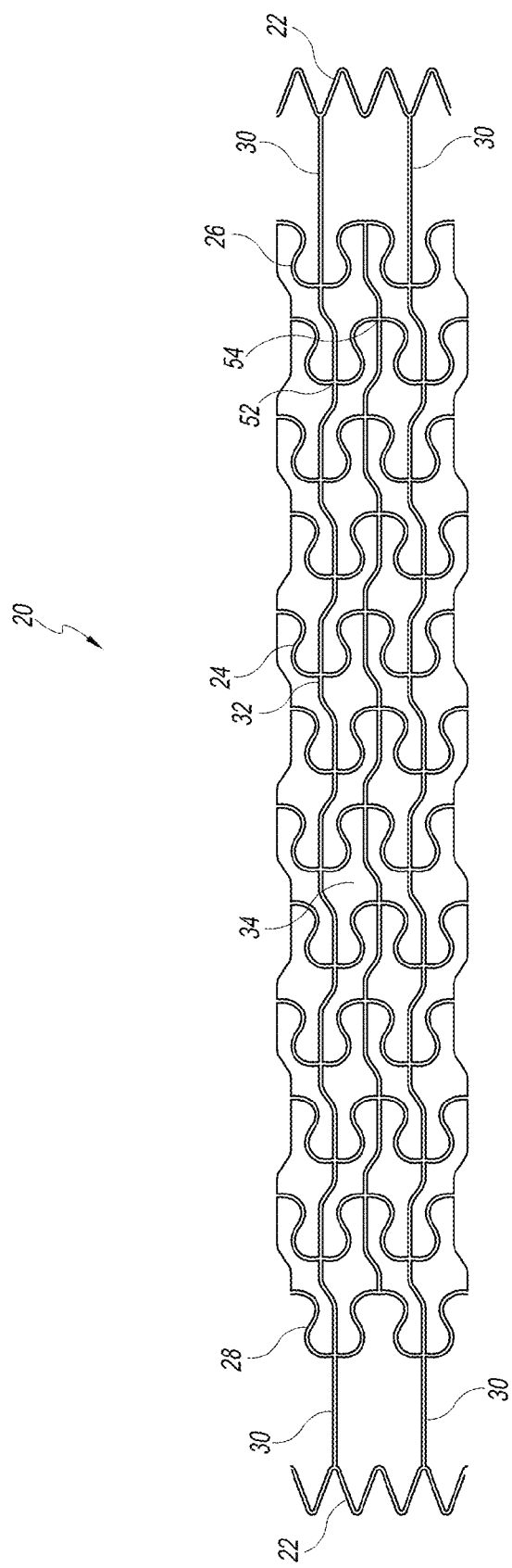

FIGS. 3a-c illustrate a CS 20 which has 3 different end ring 22-strut 30-terminal ring 26 and end ring 22-strut 30-terminal ring 28 configurations which follow the above alternating peak 52—valley 54 connection. As is further described hereinunder, each configuration provides CS 20 with unique expansion properties.

In FIG. 3a, the left side end ring 22 is connected via two struts 30 to two peaks 52, while the right side end ring 22 is connected via two struts 30 to two valleys 54 (which are offset from peaks 52 and thus are not on the same lengthwise strut 32). In such a configuration, CS 20 will want to shorten by approximately one sine amplitude when expanded by the balloon and as such, CS 20 will track with balloon expansion (balloon also shortens during expansion due to formation of pillows on its surface).

In FIG. 3b, the left side end ring 22 is connected via two struts 30 to two valleys 54, while the right side end ring 22 is connected via two struts 30 to two peaks 52 (which are offset from peaks 52 and thus are not on the same lengthwise strut 32). In such a configuration, CS 20 will want to lengthen by approximately one sine amplitude upon expansion by the balloon however since it cannot lengthen (it is fixed to catheter shaft) CS 20 will buckle at the terminal struts/rings.

In FIG. 3c, the left side end ring 22 is connected via two struts 30 to two peaks 52, while the right side end ring 22 is connected via two struts 30 to two peaks 52 (which are on the same lengthwise strut 32). In such a configuration, CS 20 will maintain the same length upon expansion and as such it might buckle at the terminal struts/rings (see the Examples section for further detail).

System 10 can be fabricated using conventional balloon catheter components, such as metallic hypotube and/or polymer tubes for fabrication of the catheter shaft, an inflation hub at the proximal end, a polymeric guide wire lumen adapted to receive the guide wire, and an inflatable balloon 16 at its distal end. The balloon catheter components are attached to each other using techniques that are known in the art such as thermal bonding and adhesives.

CS 20 is preferably fabricated using laser cutting technique in which the CS pattern is cut from a Nitinol tube. CS 20 can then be electropolished and heat treated to form an inner diameter smaller than that of the folded balloon. CS 20 is mounted over balloon 16 and positioned relatively to the balloon such that rings 24 are positioned over the working length of balloon 16 (balloon cylindrical section in between the balloon tapers) and end rings 22 are positioned over the catheter shaft or balloon legs on both sides of balloon 16. End rings 22 are thermally bonded to the catheter shaft or the balloon legs.

System 20 can be used in angioplasty as follows. System 20 can be guided to the stenosed region over a guide-wire (not shown) using well known angioplasty approaches. Once in position, balloon 16 can be inflated to a point where it protrudes through CS 20 such that isolated regions of balloon 16 apply an outward radial force to the plaque. Once the region is sufficiently dilated, balloon 16 is deflated (thereby allowing the CS 20 to recover its set configuration) and system 20 is removed from the body.

Thus, the present invention provides an angioplasty system which protects the vessel wall from the shear forces caused by balloon unwrapping and radial and uneven expansion, as well as enables provision of localized higher pressure forces to specific lesion regions which are resistant, such as highly calcified expansion-resistant plaque regions.

Balloon 16 of system 20 or pillow-like regions thereof can be coated with a hydrophilic or hydrophobic coating to enhance lubricity. Alternatively, balloon 16 of system 20 or pillow-like regions thereof can be coated with a drug coating containing an antiproliferative drug such as sirolimus or paclitaxel using methods well known in the art.

As used herein the term "about" refers to ±10%.

Additional objects, advantages, and novel features of the present invention will become apparent to one ordinarily skilled in the art upon examination of the following examples, which are not intended to be limiting.

EXAMPLES

Reference is now made to the following examples, which together with the above descriptions, illustrate the invention in a non limiting fashion.

Prototype Testing

Several designs having different shaped rings and end strut attachment configurations were fabricated and tested.

Such testing demonstrated that the shape of the ring loop is critical for achieving expansion of balloon and constraining structure and balloon constraint without ring failure and that the end strut configuration (three types shown in FIGS. 3a-c) is crucial for limiting the stress on the end struts during expansion of the constraining structure (CS).

FIGS. 4a-b illustrate two types of ring loops, one having a small radius of curvature (top loop, FIG. 4a), and the other having a relatively large radius of curvature (top loop FIG. 4b). The ring loop of FIG. 4a has a radius of 0.2 mm resulting in a loop length of approximately 0.5 mm. The ring loop of FIG. 4b has a radius of 0.5 mm, resulting in a loop length of approximately 1.5 mm.

When a ring of CS 20 expands (under balloon inflation), the radii of the peaks and valleys (formed by the zigzagging loops) grow and stresses and strains form along the radius length maximizing at the peak/valley centers.

Figure 5A:
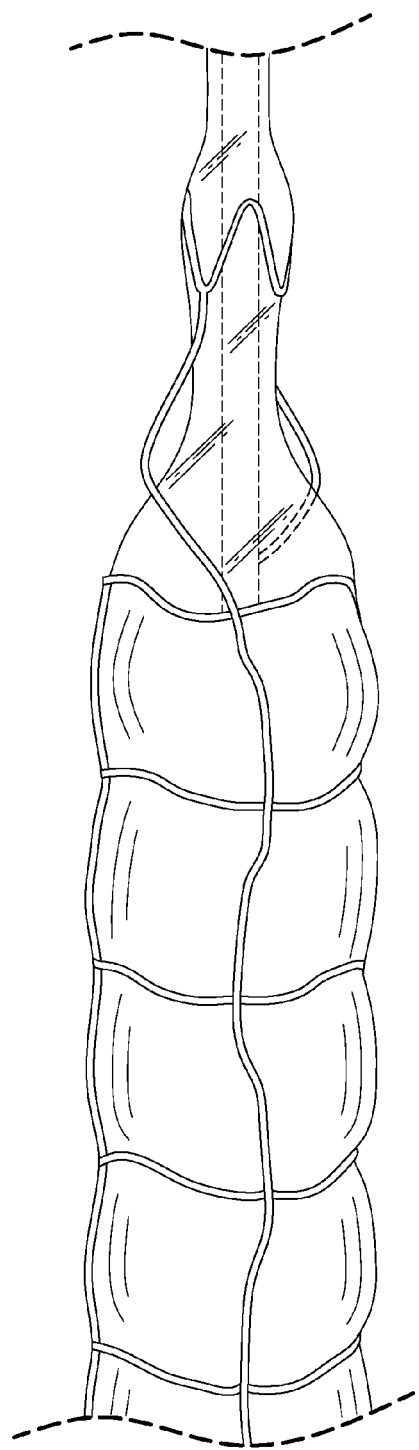
FIGS. 5a-b illustrate strut buckling (FIG. 5a) and ring failure (FIG. 5b) in an experimental prototype.
Figure 5B:
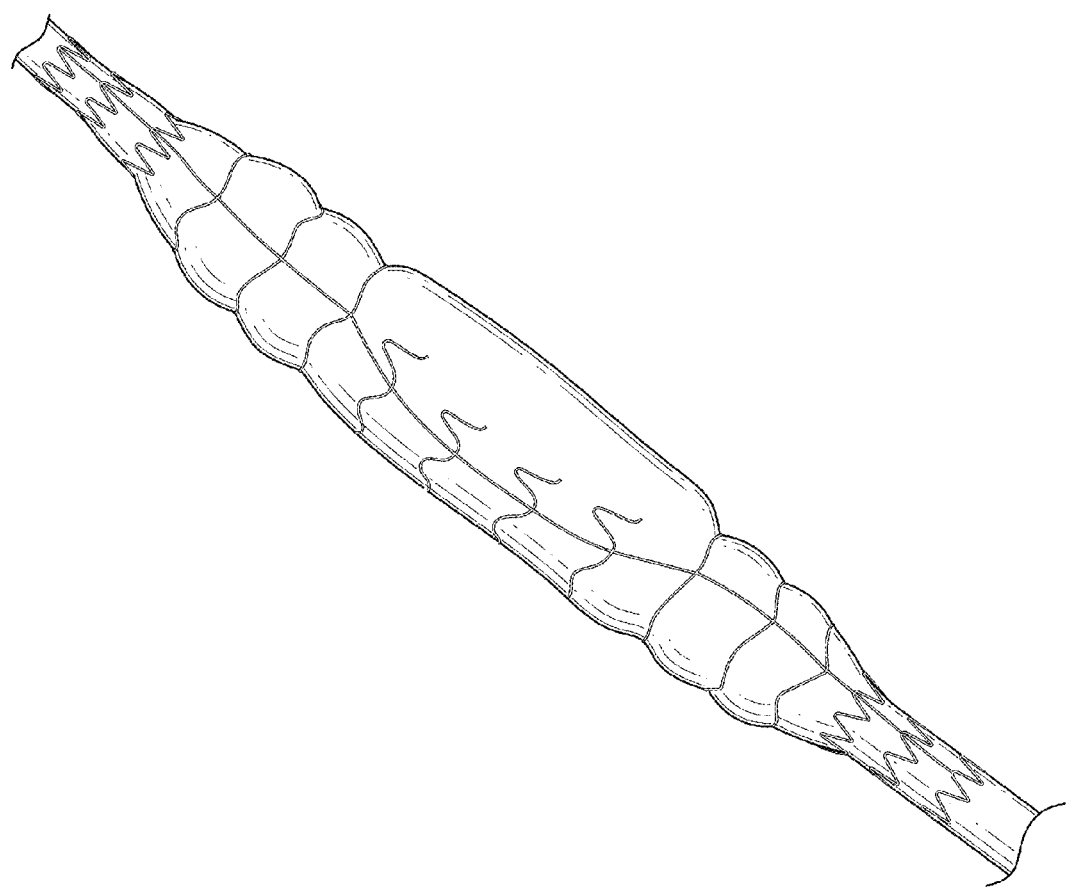

Since the loop of FIG. 4a needs to transition from a small radius to a linear structure, the strains that developed therein will be much larger than the strains on the loop of FIG. 4b which starts off having a larger radius (3×). As is shown in FIG. 5, a prototype having ring loops similar to those of FIG. 4a failed at relatively low inflation pressures (12 atm) while a prototype having loops similar to those of FIG. 4b was inflated to a pressure above 12 atm without any ring failure.

Testing of several prototypes also revealed that an end strut configuration of CS is important for maintaining CS integrity during inflation. FIG. 5a illustrates a CS having a strut configuration similar to that of FIG. 3c. As is clearly shown in this Figure, inflation of the balloon and expansion of the CS leads to buckling of the end struts (similar behavior was observed for CS having the strut configuration of FIG. 3b). In contrast, a CS having a strut configuration similar to that of FIG. 3a (CS will shorten during inflation) maintained strut-ring integrity during inflation and provided the best results.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for performing angioplasty comprising:
   (a) a balloon mounted on a catheter shaft and having a longitudinal axis; and
   (b) an expandable constraining structure including a plurality of axial struts crossing a plurality of radially-expandable rings configured for constraining said balloon such that isolated balloon regions protrude through openings in said constraining structure when said balloon is inflated,
   said expandable constraining structure being configured such that radial expansion of said radially-expandable rings does not substantially alter a distance between adjacent radially-expandable rings along said longitudinal axis,
   wherein said expandable constraining structure is configured such that radial expansion of said radially-expandable rings axially moves adjacent axial struts attached to said adjacent radially-expandable rings in opposite directions wherein said expandable constraining structure further includes first and second end rings for fixedly attaching said expandable constraining structure to the catheter shaft.

2. The system of claim 1, wherein said radially-expandable rings are configured with peaks and valleys forming an undulating omega loop path.

3. The system of claim 2, wherein said plurality of axial struts interconnect said plurality of radially-expandable rings at said peaks and said valleys.

4. The system of claim 2, wherein said undulating omega loop path comprises a plurality of contiguous omega loops.

5. The system of claim 1, comprising at least 4 axial struts crossing at least 4 radially-expandable rings, forming at least 16 of said openings.

6. The system of claim 1, wherein said first and second end rings are connected to terminal radially-expandable rings via N end struts, N being half of a number of said plurality of axial struts.

7. The system of claim 6, wherein said N end struts of said first end ring are connected to peaks of a first terminal radially-expandable ring, and said N end struts of said second end ring are connected to valleys of a second terminal radially-expandable ring.

8. The system of claim 6, wherein said N end struts of said first end ring are connected to peaks of a first terminal radially-expandable ring, and said N end struts of said second end ring are connected to peaks of a second terminal radially-expandable ring.

9. The system of claim 6, wherein N equals 2.

10. The system of claim 1, wherein said plurality of axial struts are fabricated from a super-elastic alloy having a thickness within the range of from about 0.04 to about 0.12 mm.

11. The system of claim 1, wherein said plurality of radially-expandable rings are fabricated from a super-elastic alloy having a thickness within the range of from about 0.05 to about 0.12 mm.

12. The system of claim 1, wherein said plurality of radially-expandable rings are capable of radially expanding from a compressed state of 1 mm in diameter to an expanded state of 6 mm in diameter.

13. The system of claim 1, wherein said plurality of radially-expandable rings form an undulating radial path when compressed and a substantially linear radial path when expanded.

14. The system of claim 1, wherein a length of said expandable constraining structure from said first end ring to said second end ring is within the range of from about 5 mm to about 300 mm.

15. The system of claim 1, wherein said isolated balloon regions protrude about 0.1-0.5 mm from an outer surface of said expandable constraining structure.

16. The system of claim 1, wherein said balloon is coated with a drug.

17. The system of claim 16, wherein said drug coating contains a drug or a drug and one or more excipients.

18. The system of claim 17, wherein said drug is an antiproliferative drug.

19. The system of claim 16, wherein said drug coating is coated on said isolated balloon regions that protrude through said openings.

20. The system of claim 19, wherein said isolated balloon regions protruding through said openings are about 1-5 mm in length and about 1-3.5 mm in width.

21. A method of treating a body vessel comprising:
   (a) positioning, in the vessel, a balloon disposed within an expandable constraining structure including a plurality of axial struts crossing a plurality of radially-expandable rings configured for constraining said balloon such that isolated balloon regions protrude through openings in said expandable constraining structure when said balloon is inflated;

said expandable constraining structure being configured such that radial expansion of said radially-expandable rings:
  (i) does not substantially alter an axial distance between adjacent radially-expandable rings; and
  (ii) axially moves adjacent axial struts attached to said adjacent radially-expandable rings in opposite directions; and (b) inflating said balloon so as to enable said isolated balloon regions to protrude through said openings and contact a wall of the vessel while said plurality of axial struts and said plurality of radially-expandable rings are displaced from the vessel, thereby treating the body vessel.

22. The method of claim 21, wherein (b) is effected by inflating said balloon to at least 3 atm.

23. The method of claim 21, wherein the vessel is an artery and the treatment is angioplasty.

* * * * *